(12) United States Patent
Zimmerman et al.

(10) Patent No.: US 8,754,084 B2
(45) Date of Patent: Jun. 17, 2014

(54) THERAPEUTIC METHODS AND AGENTS FOR TREATING MYOTONIC DYSTROPHY

(71) Applicant: The Board of Trustees of the University of Illinois, Urbana, IL (US)

(72) Inventors: Steven C. Zimmerman, Champaign, IL (US); Chun-Ho Wong, Champaign, IL (US); Paul J. Hergenrother, Champaign, IL (US); Jessie Peh, Urbana, IL (US)

(73) Assignee: The Board of Trustees of the University of Illinois, Champaign, IL (US)

( * ) Notice: Subject to any disclaimer, the term of this patent is extended or adjusted under 35 U.S.C. 154(b) by 0 days.

(21) Appl. No.: 13/851,829

(22) Filed: Mar. 27, 2013

(65) Prior Publication Data

US 2013/0261124 A1 Oct. 3, 2013

Related U.S. Application Data

(60) Provisional application No. 61/616,165, filed on Mar. 27, 2012.

(51) Int. Cl.
*A61K 31/53* (2006.01)
*C07D 403/00* (2006.01)

(52) U.S. Cl.
USPC .......................................... 514/245; 544/198

(58) Field of Classification Search
USPC .......................................... 514/245; 544/198
See application file for complete search history.

(56) References Cited

U.S. PATENT DOCUMENTS

| | | | |
|---|---|---|---|
| 5,834,451 | A | 11/1998 | Ohsawa et al. |
| 6,987,123 | B2 | 1/2006 | Lohray et al. |
| 7,589,123 | B2 | 9/2009 | Rees et al. |
| 7,704,951 | B2 | 4/2010 | Hirashima et al. |

OTHER PUBLICATIONS

David et al., "DNA Mismatch-Specific Base Flipping by a Bisacridine Macrocycle," ChemBioChem (2003) 4: 1326-1331.
Gareiss et al., "Dynamic Combinatorial Selection of Molecules Capable of Inhibiting the (CUG) Repeat RNA-MBNL1 Interaction in Vitro: Discovery of Lead Compounds Targeting Myotonic Dystrophy (DM1)," J. Am. Chem. Soc. (2008) 130: 16254-16261.
Mooers et al., "The structural basis of myotonic dystrophy from the crystal structure of CUG repeats," PNAS (Nov. 15, 2005) 102 (46): 16626-16631.
Wong, "Discovery of Small Molecule Inhibitors of MBNL RNA Interaction: Toward Therapeutic Agents to Treat Myotonic Dystrophy," The Chinese University of Hong Kong (presentation Jan. 4, 2012).
Wong et al., "Selective inhibition of MBNL1-CCUG interaction by small molecules toward potential therapeutic agents for myotonic dystrophy type 2 (DM2)," Nucleic Acids Research (2011) 39 (20): 8881-8890.
Arambula et al., "A simple ligand that selectively targets CUG trinucleotide repeats and inhibits MBNL protein binding," PNAS (Sep. 22, 2009) 106 (38): 16068-16073.

*Primary Examiner* — Jeffrey H Murray
*Assistant Examiner* — Oluwafemi Masha
(74) *Attorney, Agent, or Firm* — Haukaas Fish PLLC; Michael H. Haukaas

(57) ABSTRACT

The invention provides compounds, compositions and methods for treating myotonic dystrophy. The compounds can selectively bind to CUG repeats in RNA, or to CTG repeats in DNA, and inhibit replication of the nucleic acids.

20 Claims, 5 Drawing Sheets

THERAPEUTIC METHODS AND AGENTS FOR TREATING MYOTONIC DYSTROPHY

RELATED APPLICATIONS

This application claims priority under 35 U.S.C. §119(e) to U.S. Provisional Patent Application No. 61/616,165, filed Mar. 27, 2012, which is incorporated herein by reference.

GOVERNMENT SUPPORT

This invention was made with government support under contract number R01AR058361 awarded by the National Institutes of Health. The government has certain rights in the invention.

BACKGROUND OF THE INVENTION

Myotonic dystrophy (DM or Steinert's disease) is a multisystemic disorder often characterized by muscle degeneration and myotonia or delayed muscle relaxation due to repetitive action potentials in myofibers. Numerous multisystemic symptoms are observed in DM patients, including over 100 biological processes negatively affected in their muscle cells. Manifestations of DM can include heart conduction defects, ocular cataracts, hypogonadism, and nervous system dysfunction. DM patients also often suffer from cardiac conduction defects, smooth muscle involvement, hypersomnia, cataracts, abnormal glucose response, and, in males, premature balding and testicular atrophy. Myotonic dystrophy is the most common muscular dystrophy of adults for which there are no effective therapies.

Myotonic dystrophy type 1 (DM1) is the most common form of muscular dystrophy, affecting about 1 in 8000 people. DM1 is a trinucleotide repeat expansion disorder (TREDs) with $(CTG)_n$ step sequences aberrantly expanded in the 3'-untranslated region of the DMPK gene. At the RNA level, the DMPK transcript sequesters splicing regulator proteins, in particular muscleblind-like (MBNL) protein, which results in incorrect splicing of a number of pre-mRNAs, and this gain-of-function is the direct cause of DM1. A drug that binds to CUG repeats, thereby freeing MBNL to regulate splicing of its pre-mRNA targets, could provide a successful therapeutic strategy. Alternatively, binding looped out $(CTG)_n$ repeats may inhibit transcription of the expanded region or even reduce the expansion during repair or replication. Accordingly, agents and therapeutic agents that selectively bind MBNL protein and treat myotonic dystrophy are needed to bolster the clinical therapy of these disorders.

SUMMARY

The invention provides selective, non-toxic, small-molecule ligands as practical therapeutic agents for inhibiting toxic protein-RNA interactions, for example, MBNL1-RNA interactions. Currently known inhibitor candidates are not highly selective, are toxic, or are less effective than the inhibitors described herein. A new series of small molecules that inhibit MBNL1-RNA interaction have been designed, prepared, and evaluated. The ligands can also inhibit other biological processes in vitro or in vivo with very low toxicity and high selectivity and efficacy.

The compounds described herein show efficacy for inhibiting MBNL1-RNA interaction and restoring proteins associated with important misspliced mRNAs. The compounds are non-toxic as demonstrated in numerous cell cultures, and the compounds are easily synthesized from low-cost commercially available materials. The invention also provides inexpensive methods to prepare safe and effective therapeutic agents for treating myotonic dystrophy.

Accordingly, the invention therefore provides compounds of Formula (I):

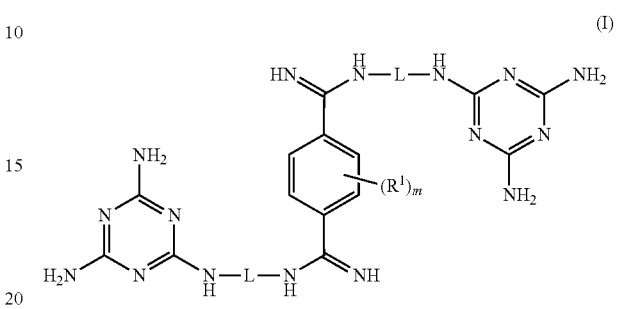

(I)

wherein m is 0, 1, 2, 3, or 4;

each $R^1$ is independently alkyl, cycloalkyl, aryl, heteroaryl, heterocycle, halo, hydroxyl, nitro, cyano, alkoxy, carboxy, trifluoromethyl, trifluoromethoxy, amino, or aminoalkyl; and each L is independently a divalent alkyl or a divalent radical of the formula —W-A-W— wherein each W is independently —N(R")C(=O)—, —C(=O)N(R")—, —OC(=O)—, —C(=O)O—, —S(O)—, —S(O)$_2$—, —N(R")—, —C(=O)—, —(CH$_2$)$_n$— where n is 1-10, or a direct bond; wherein each R" is independently H, (C$_1$-C$_6$)alkyl, or a nitrogen protecting group; and A is (C$_1$-C$_{20}$)alkyl, (C$_2$-C$_{16}$)alkenyl, (C$_2$-C$_{16}$)alkynyl, (C$_3$-C$_8$)cycloalkyl, (C$_1$-C$_{20}$)heteroalkyl, (C$_6$-C$_{10}$)aryl, —(OCH$_2$—CH$_2$)$_n$— where n is 1 to about 20, —C(O)NH(CH$_2$)$_n$ wherein n is 1 to about 6, —N(Me)(CH$_2$)$_n$ wherein n is 1 to about 6; or (C$_1$-C$_{20}$)alkyl, (C$_2$-C$_{16}$)alkenyl, (C$_2$-C$_{16}$)alkynyl, or —(OCH$_2$—CH$_2$)$_n$-interrupted between two carbons, or between a carbon and an oxygen, with a heterocycle, or (C$_6$-C$_{10}$)aryl group; or a pharmaceutically acceptable salt thereof.

In one embodiment, L is (C$_1$-C$_{12}$)alkyl. In another embodiment, L can be (C$_2$-C$_{12}$)alkyl, (C$_3$-C$_{12}$)alkyl, (C$_3$-C$_{10}$)alkyl, (C$_4$-C$_{12}$)alkyl, (C$_2$-C$_5$)alkyl, or (C$_3$-C$_4$)alkyl. In yet another embodiment, L can be an alkyl of 1, 2, 3, 4, 5, 6, 7, 8, 9, 10, 11, or 12 carbon atoms in length, optionally interrupted with one or more oxygen atoms, and optionally substituted with a substituent described herein.

In one embodiment, L is —CH$_2$—(OCH$_2$—CH$_2$)$_n$—OCH$_2$— where n is 1 to about 20. In another embodiment, L is —CH$_2$—CH$_2$—(OCH$_2$—CH$_2$)$_n$—OCH$_2$—CH$_2$— where n is 1 to about 20. The variable n can be any integer from 1 to 20, or any range of integers from any one integer from 1 to 20 to any other integer from 1 to 20.

In one embodiment, m is 0. In other embodiments, m can be 1, 2, 3 or 4.

$R^1$ can be a variety of groups such as the substituents described herein. In some embodiments, $R^1$ can be methyl, ethyl, cyclopropyl, phenyl, benzyl, pyridyl, furanyl, F, Cl, Br, OH, NO$_2$, CN, methoxy, ethoxy, carboxy, trifluoromethyl, trifluoromethoxy, amino, or methylamino.

The compound of Formula (I) can be a compound of Formula (II):

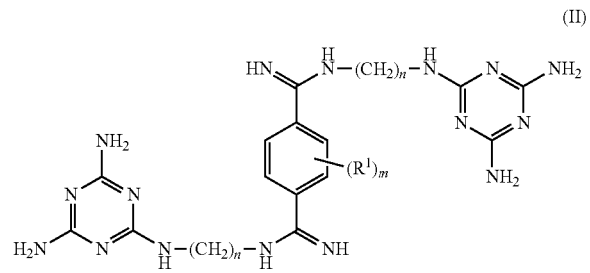

(II)

wherein
each n is independently 3, 4, 5, 6, 7, 8, 9, or 10; and $R^1$ and m are as defined for Formula I; or a pharmaceutically acceptable salt thereof. In one embodiment, the compound of Formula (II) is a compound of Formula (III):

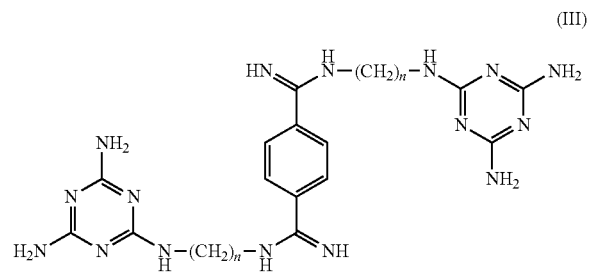

(III)

wherein
each n is independently 3, 4, or 5; or a pharmaceutically acceptable salt thereof.

The invention also provides compositions comprising a compound described herein and a pharmaceutically acceptable diluent or carrier. The composition can be used to treat a medical condition, such as myotonic dystrophy. The myotonic dystrophy can be, for example, myotonic dystrophy type 1 (DM1) or myotonic dystrophy type 2 (DM2). The compound or composition can also be used for complexing with CUG repeats in RNA, for example, in RNA analysis and clinical research. The complexing can have a variety of uses including inhibiting the replication of the RNA.

The invention also provides a method for treating myotonic dystrophy comprising administering to a patient in need thereof an effective amount of a compound described herein, wherein the administration thereby treats or reduces the symptoms of the myotonic dystrophy. In some embodiments, the myotonic dystrophy is myotonic dystrophy type 1 (DM1).

The invention further provides a method to inhibit muscleblind-like (MBNL) protein binding comprising contacting MBNL protein with an effective inhibitory amount of a compound described herein, whereby the contacting inhibits the activity of the MBNL protein.

The invention further provides a method to selectively form a complex with CUG repeats in RNA, or CTG repeats in DNA, comprising contacting the RNA or DNA with a compound described herein, thereby forming a complex of the compound and the RNA, or a complex of the compound and the DNA, wherein the complexation inhibits RNA replication or DNA replication. The affinity of the compound for the CUG repeat in RNA can be, for example, less than about 2 micromolar, less than about 1.5 micromolar, less than about 1 micromolar, less than about 900 nM, less than about 800 nM, less than about 750 nM, or less than about 500 nM.

The invention provides novel compounds of the formulas described herein, intermediates for the synthesis of the compounds and formulas, as well as methods of preparing the compounds and formulas. The invention also provides compounds that are useful as intermediates for the synthesis of other useful compounds. The invention provides for the use of compounds of the formulas described herein for the manufacture of medicaments for use in medical therapy. Thus, the invention provides for the use of the compounds and compositions described herein for the treatment of various conditions including myotonic dystrophy, related conditions, and the symptoms of such conditions. The invention also provides for the use of a compound or composition as described herein for the manufacture of a medicament to treat a disease in a mammal, for example, myotonic dystrophy in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

One of the main causes of myotonic dystrophy (DM) is the sequestration of an important protein, MBNL1, by abnormally long RNAs. This sequestration restricts the protein activity, which can lead to the many symptoms of DM. A key therapeutic approach provided by this disclosure is the release of MBNL1 from the RNA using small-molecule drugs. This invention provides effective ligands ("active agents") to inhibit the toxic protein-RNA interaction, thereby providing a therapy for the disease.

In some embodiments, the disclosure provides molecules for the treatment of myotonic dystrophy. In other embodiments, the disclosure provides methods for making the molecules, methods for making pharmaceutical derivatives of the molecules, and various methods for treating DM and inhibiting the binding of proteins such as MBNL1.

The ligands described herein have significant advantageous therapeutic properties, including the ability to inhibit MBNL1-RNA interaction and to restore proteins associated with important misspliced mRNAs. The compounds can be readily synthesized, for example, in 3-synthetic steps from low-cost and commercially available starting materials. In certain embodiments, this disclosure provides an inexpensive method to prepare effective and safe therapeutic agents for use in the treatment of patients with myotonic dystrophy.

In developing a ligand to target the CUG or CTG repeat, the weakly paired U-U or T-T mismatch presents one opportunity for recognition by hydrogen bonding. Although there are small molecules capable of hydrogen bond-mediated, selective recognition of the G-G, C-C, or A-A mismatch, there is currently no known, high affinity binder that is selective for T-T or U-U mismatches. In fact, there have been very few ligands found to recognize CUG or CTG repeat sequences (see Arambula et al., PNAS 2009, 106(38), 16068-16073).

Actinomycin D has been reported to bind $(CTG)_n$ repeats, while a macrocyclic diacridine has been shown to bind mismatches containing a T with low specificity. A combinatorial screening approach was used to identify peptide ligands that bind to CUG repeat sequences with modest 5-10-fold selectivity over duplex structures. These ligands may also be limited by their relatively high molecular weights and peptidic structure.

The invention thus provides compound 1, a simple triaminotriazine-acridine conjugate designed to hydrogen bond to both U's or T's in the U-U or T-T mismatch, which selectively binds CTG and CUG repeats with high nanomolar affinity and inhibits the binding of a protein comprised of the RNA binding region of MBNL1 (MBNL1N, amino acids 1-272) to $(CUG)_4$ and $(CUG)_{12}$ RNAs with low micromolar $K_i$ values in the presence of competitor tRNA.

Figure 1:
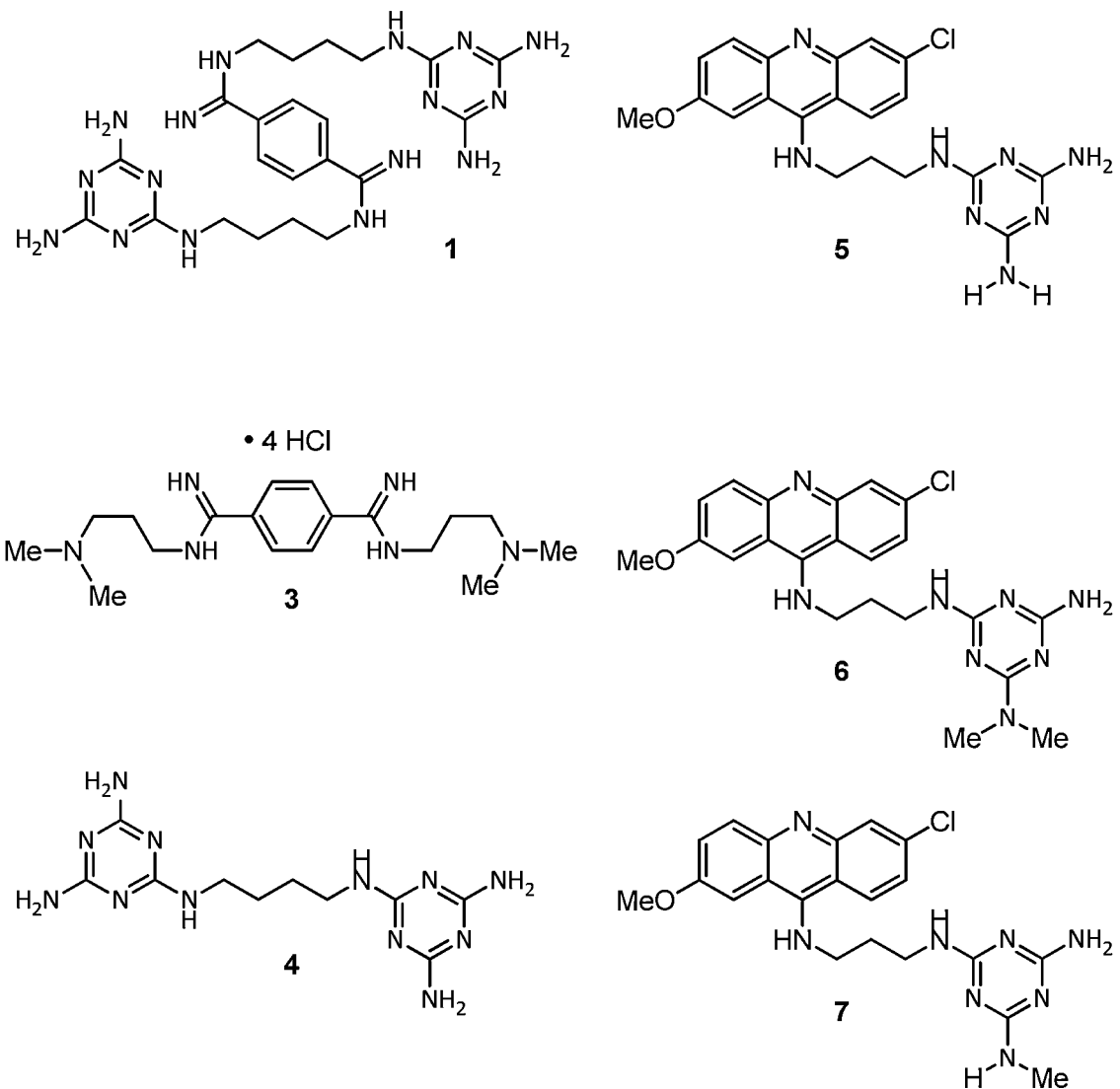
FIG. 1. Structures of select compounds tested by electrophoretic mobility shift assay (EMSA).
Figure 2:
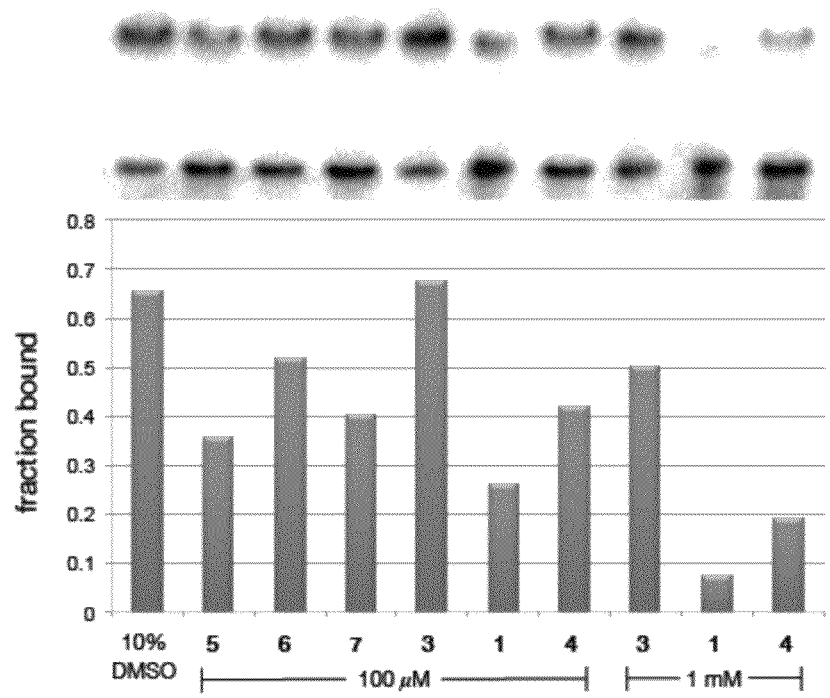
FIG. 2. EMSA screening of compounds at concentrations of 1 mM and 100 µM.
Figure 3:
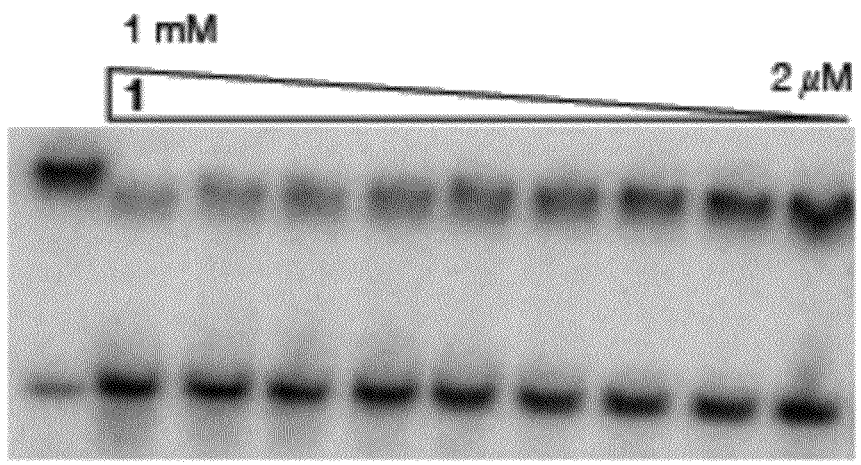
FIG. 3. Concentration-dependent EMSA of inhibition of MBNL1-CUG interaction by compound 1.

The drug performance of certain compounds was evaluated both in vitro and ex vivo. An electrophoretic mobility shift assay (EMSA) screen compared the binding of certain compounds (e.g., compounds 3-7) with compound 1 (FIG. 2). It was found that compound 1 showed a significantly improved inhibitory ability when compared to other inhibitor compounds (such as compound 5) at the same concentration (100 μM). The improved water solubility of compound 1 also allowed us to test the inhibition without using DMSO and at a higher concentration (1 mM) than has been possible with other compounds (FIG. 3). The inhibition constant (Ki) of compound 1 for MBNL1-CUG interaction was determined to be 177 nM ($IC_{50}$=11 μM).

Figure 4:
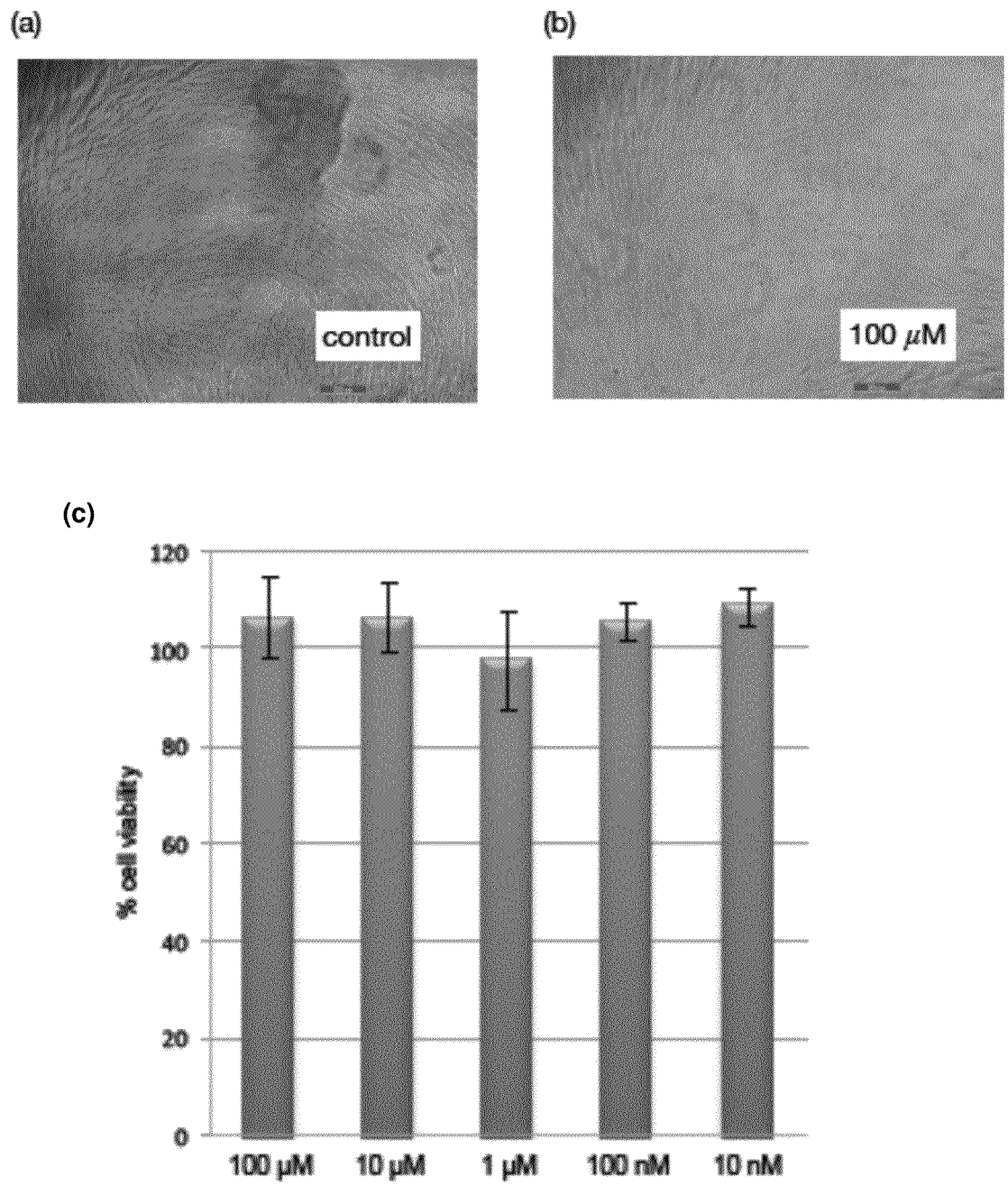
FIG. 4. (a) 3T3 mouse fibroblast without treatment showing the fibrous morphology. (b) After treatment with 100 µM of compound 1 for 3 days. (c) Percentage cell viability plot.

Compound 1 was also found to be non-toxic towards mouse fibroblasts (FIG. 4a, b). No toxicity (100% cell viability) was observed even with treatment of 100 μM of compound 1 during 3-day incubation (FIG. 4c). Similar non-toxicity was observed for HeLa and DM1 cells.

Figure 5:
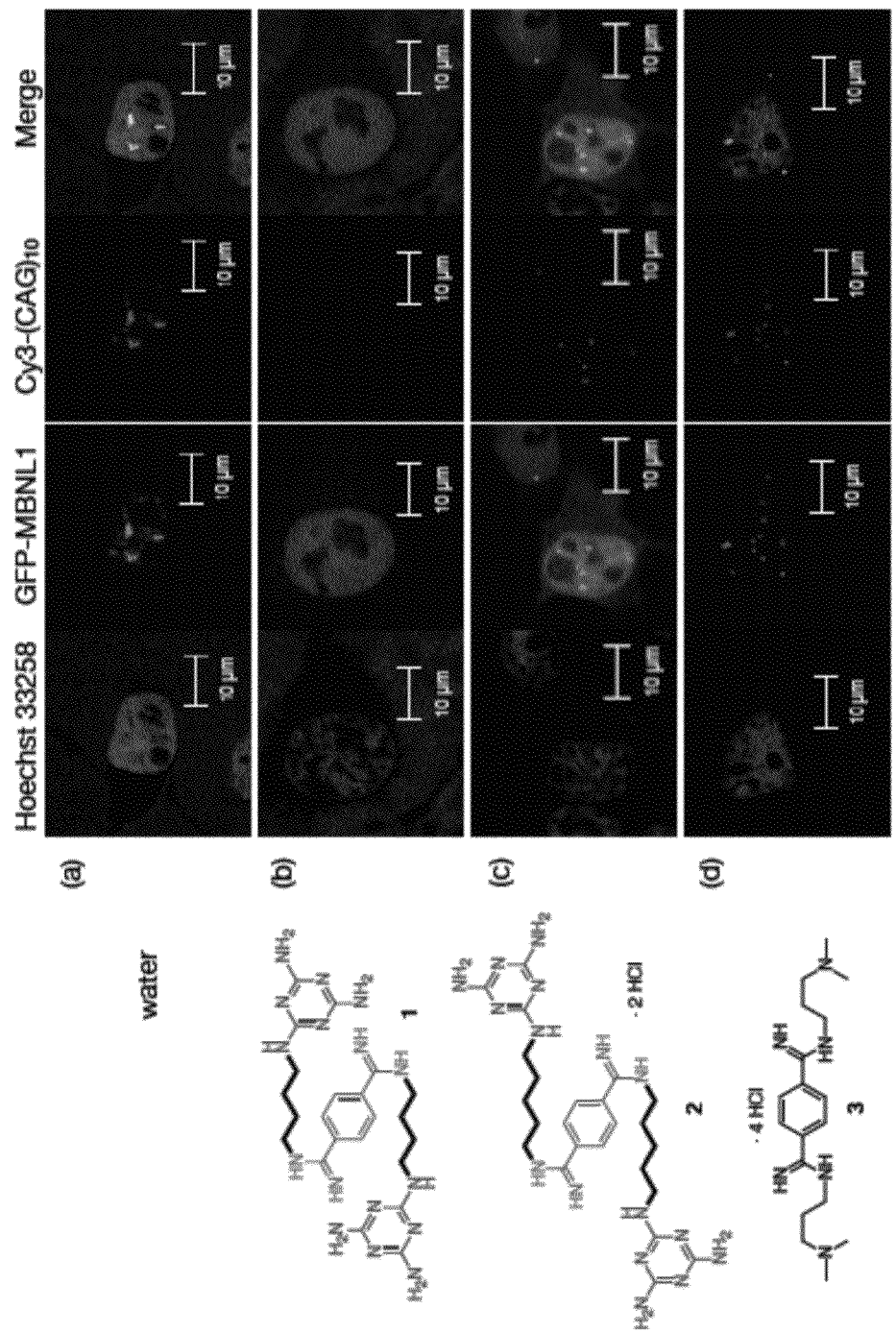
FIG. 5. (a) Confocal microscopy showing HeLa cells containing $(CUG)_{960}$ repeats sequestered MBNL1 as foci inside the nucleus. (b and c): Compound 1 and 2 showed significant disruption of foci as dispersed green signals. (d) Negative control compound 3 showed no inhibition, foci remained.

In various embodiments, the compounds described herein can form MBNL1-CUG foci inside the nucleus for cells containing expanded CUG repeats. Using confocal microscopy, preliminary results have demonstrated that HeLa cells transfected with the GFP-MBNL1 gene and DMPK gene containing $(CUG)_{960}$ showed co-localization of MBNL1 and CUG repeats inside the nucleus (FIG. 5a). Compounds 1 and 2 (with $(CH_2)_4$ and $(CH_2)_5$ tethers for the diamine linker (e.g., butane-1,4-diamine and pentane-1,5-diamine derived linkers), respectively) showed significant disruption of MBNL1-CUG foci as a dispersed green signal in the nucleus (FIG. 5b,c). Even fewer foci were observed with compound 1 when compared to compound 2. Compound 3, as a negative control, did not show any disruption of foci (FIG. 5d).

Figure 6:
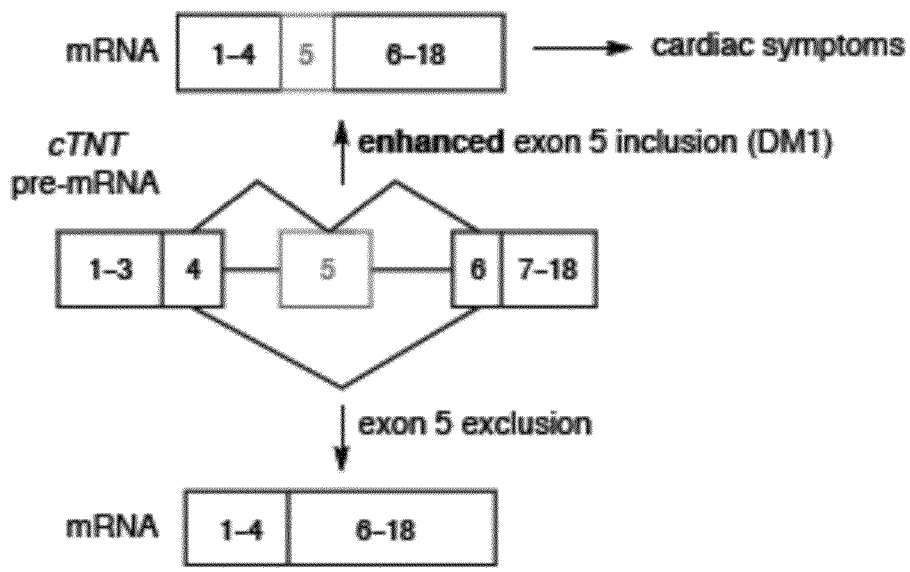
FIG. 6. (a) Alternative splicings of cTNT pre-mRNA. In DM1 cells, exon 5 inclusion is enhanced and led to cardiac symptoms in DM patients. (b) Partial rescuing of missplicing by compounds 1 and 2 but not 3.
Figure 6:
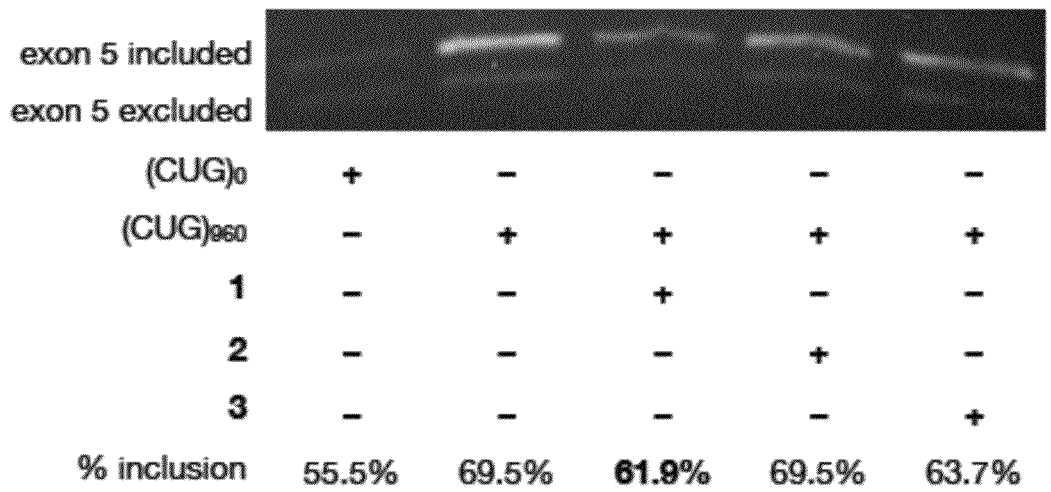

Another feature of DM that is the mis-regulated splicing of multiple pre-mRNAs because of the sequestration of MBNL1, alternate splicing regulator, by expanded CUG repeats (FIG. 6a). In DM1 cells, exon 5 inclusion is enhanced due to the MBNL1 sequestration which leads to a change in production ratio of the two cTNT mRNAs (normally 55.5% to 69.5%; lanes 1 and 2 in FIG. 6b). Compounds 1 and 2 were capable of reducing the percentage to 61.9% and 63.7%, respectively (lanes 3 and 5). In good agreement with the results from confocal microscopy, compound 1 is more effective than compound 2. Again, compound 3 showed no improvement in rescuing the mis-regulated splicing (lane 4). Accordingly, the invention provides methods for reducing exon 5 inclusion by reducing MBNL1 sequestration.

Compounds of the invention have been prepared and tested both in vitro and ex vivo after the conceptual design. The syntheses have been optimized and are scalable from milligram- to gram-scale in good yields and purity without difficulties. The compounds are water-soluble and are shown to be active by electrophoretic mobility shift assay and confocal microscopy evaluation. More importantly, the compounds showed rescuing of the mis-regulated splicing cTNT pre-mRNA.

The compounds are found to be non-toxic among different cell types tested, including DM1 patient cells and 3T3 mouse fibroblasts. In one experiment, three mice each were evaluated at 5, 10, 20 50, and 100 mg/kg of compound 1, given by intraperitoneal injection. The maximum tolerated dose was found to be 50 mg/kg. Only at concentrations of 100 mg/kg did mice exhibit neurotoxicity (two of three, while the third still did not exhibit signs of neurotoxicity).

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R.J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and sub-combinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups (groups from which a proton can be removed (e.g., —COOH) or added (e.g., amines) or which can be quaternized (e.g., amines)). All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Whenever a range is given in the specification, for example, a temperature range, a time range, a carbon chain range, or a composition or concentration range, all intermediate ranges and subranges, as well as all individual values included in the ranges given are intended to be individually included in the disclosure. It will be understood that any subranges or individual values in a range or subrange that are included in the description can be optionally excluded from embodiments of the invention.

Specific values listed below for radicals, substituents, and ranges, are for illustration only; they do not exclude other defined values or other values within defined ranges for the radicals and substituents. However, certain values or ranges of values can optionally be excluded from certain embodiments in the form of negative limitations.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl(iso-propyl), 1-butyl, 2-methyl-1-propyl(isobutyl), 2-butyl(sec-butyl), 2-methyl-2-propyl(t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furanyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like. Various combinations of the aforementioned positions are included in the compounds described herein.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano. Additionally, suitable substituent groups can be, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —OP(=O)(OH)(OR), —P(=O)(OH)(OR), —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

The term "interrupted" indicates that another group is inserted between two adjacent carbon atoms (and the hydrogen atoms to which they are attached (e.g., methyl ($CH_3$), methylene ($CH_2$) or methine (CH))) of a particular carbon chain being referred to in the expression using the term "interrupted, provided that each of the indicated atom's normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl ($SO_2$). Alkyl groups can be interrupted by one ore more (e.g., 1, 2, 3, 4, 5, or about 6) of the aforementioned suitable groups. The site of interruption can also be between a carbon atom of an alkyl group and a carbon atom to which the alkyl group is attached. An alkyl group that is interrupted by a heteroatom therefor forms a heteroalkyl group.

The term "heteroalkyl," by itself or in combination with another term, means, unless otherwise stated, a stable straight or branched chain, or cyclic hydrocarbon radical, or combinations thereof, consisting of at least one carbon atom and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule or formula. Thus, a heteroalkyl group can be a straight- or branched-chain alkyl group having about 2 to about 14 carbons, often 2 to 10 carbons in the chain, one or more of which has been replaced by a heteroatom. Exemplary heteroalkyls include alkyl ethers, secondary and tertiary alkyl amines, amides, alkyl sulfides, and the like. The group may be a terminal group or a bridging group when divalent. Examples of heteroalkyl groups include, but are not limited to, —CH$_2$—CH$_2$—O—CH$_3$, —CH$_2$—CH$_2$—NH—CH$_3$, —CH$_2$—CH$_2$—N(CH$_3$)$_2$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)$_2$, —O—CH$_3$, —O—CH$_2$—CH$_3$, and —CN.

The term "alcohol" as used herein may be defined as an alcohol that comprises a $C_{1-12}$ alkyl moiety substituted on carbon with a hydroxyl group. Alcohols include ethanol, n-propanol, i-propanol, n-butanol, i-butanol, s-butanol, t-butanol, n-pentanol, i-pentanol, n-hexanol, cyclohexanol, n-heptanol, n-octanol, n-nonanol, n-decanol, and the like. The carbon atoms in alcohols can be straight, branched or cyclic. Alcohols can be used as solvents or reagents for various reactions described herein, and hydroxyl and alkoxy groups can be substituents of the various compounds and formulas described herein.

The term "alkoxy" refers to the group alkyl-O—, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The terms "acyl" and "alkanoyl" refer to groups of the formula —C(=O)R, wherein R is an alkyl group as previously defined. The term "aroyl" refers to groups of the formula —C(=O)Ar, wherein Ar is an aryl group as previously defined.

The term "alkoxycarbonyl" refers to groups of the formula —C(=O)OR, wherein R is an alkyl group as previously defined.

The term "alkoxyacyl" refers to groups of the formula —C(=O)—OR, wherein R is alkyl as previously defined. Examples of alkoxyacyl groups include methoxyacetyl and ethoxyacetyl.

The term "acyloxy" refers to groups of the formula —O—C(=O)R, wherein R is an alkyl group as previously defined. Examples of acyloxy groups include acetoxy and propanyloxy.

The term "amino" refers to —NH$_2$, and the term "alkylamino" refers to —NR$_2$, wherein at least one R is alkyl and the second R is hydrogen, alkyl, a nitrogen protecting group or a substituent as described herein. The term "acylamino" refers to RC(=O)NH—, wherein R is as described previously.

Substituents can include cycloalkylalkyl groups. "Cycloalkylalkyl" may be defined as a cycloalkyl-alkyl-group in which the cycloalkyl and alkyl moieties are as previously described. Exemplary monocycloalkylalkyl groups include cyclopropylmethyl, cyclopentylmethyl, cyclohexylmethyl and cycloheptylmethyl.

The term "exposing" is intended to encompass the term as broadly understood in the art. In an embodiment, the term means to subject or allow to be subjected to an action, influence, or condition. For example and by way of example only, a cell can be subjected to the action, influence, or condition of a therapeutically effective amount of a pharmaceutically acceptable form of a therapeutic agent.

The term "contacting" refers to the act of touching, making contact, or of bringing to immediate or close proximity (i.e., exposing), including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. A "therapeutically effective amount" of a compound with respect to the subject method of treatment refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated, e.g., at a reasonable benefit/risk ratio applicable to any medical treatment.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate. The term "treating" or "treatment" thus can include reversing, reducing, or arresting the symptoms, clinical signs, and underlying pathology of a condition in manner to improve or stabilize a subject's condition.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The phrase "maximum tolerated dose" is employed herein to refer to the highest dose of a pharmacological treatment that will produce the desired effect without unacceptable toxicity.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, *Remington's Pharmaceutical Sciences*, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

General Synthetic Methods

The invention also relates to methods of making the compounds and compositions of the invention. The compounds and compositions can be prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5th Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis*, Second Edition, Cary and Sundberg (1983); *Protecting Groups in Organic Synthesis*, Second Edition, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compositions of the invention are provided below. These methods are intended to illustrate the nature of such preparations are not intended to limit the scope of applicable methods. Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be $-100°$ C. to $200°$ C., solvents will be aprotic or protic, depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about $20°$ C.), although for metal hydride reductions frequently the temperature is reduced to $0°$ C. to $-100°$ C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures ($0°$ C. to $-100°$ C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group that, when bound to a hydroxyl, nitrogen, or other heteroatom, prevents undesired reactions from occurring at the sight of the heteroatom, and which group can be removed by conventional chemical or enzymatic steps to reestablish the 'unprotected' hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product. The $R^1$ groups of Formula (I) can also be protecting groups, as described herein.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, New York, 1994), which is incorporated herein by reference in its entirety. Some specific protecting groups that can be employed in conjunction with the methods of the invention are discussed below.

Protecting groups do not need to be, and often are not, the same if the compound is substituted with multiple PGs. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art. For further detail regarding carboxylic acid protecting groups and other protecting groups for acids, see Greene, cited above. Such groups include by way of example and not limitation, esters, amides, hydrazides, and the like.

Typical nitrogen protecting groups described in Greene (pages 14-118) include benzyl ethers, silyl ethers, esters including sulfonic acid esters, carbonates, sulfates, and sulfonates. For example, suitable nitrogen protecting groups include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido);

silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl);

esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate (mesitoate));

carbonates(methyl, 9-fluorenylmethyl, ethyl, 2,2,2-trichloroethyl, 2-(trimethylsilyl)ethyl, 2-(phenylsulfonyl) ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate);

groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy) ethyl carbonate, 4-(methylthiomethoxy)butyrate; and miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tiglate), o-(methoxycarbonyl)benzoate, p-poly-benzoate, a-naphthoate, nitrate, alkyl N,N,N',N'-tetramethyl-phosphorodiamidate, n-phenylcarbamate, borate, 2,4-dinitrophenylsulfenate); and sulfonates (sulfate, methanesulfonate (mesylate), benzylsulfonate, tosylate, triflate).

Compound Preparation

These small molecule drugs described herein can be prepared by using inexpensive, commercially available materials in as few as three synthetic steps and only a single chromatographic purification step. Importantly, the final active agents have been found to be highly water-soluble. Scheme 1 shows a synthetic scheme for the preparation of ligand A from commercially available starting materials.

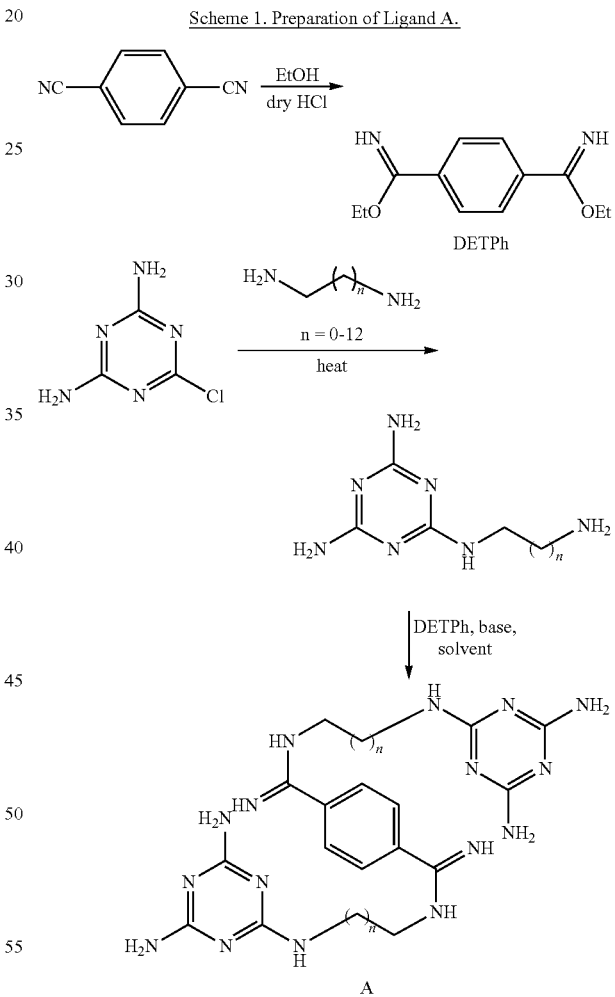

The terephthalonitrile starting material can be optionally substituted with one to four substituents, as described above in the definition of substituents, to provide ligand A with a substituted central core. Numerous substituted terephthalonitriles are commercially available, or they can be prepared standard synthetic transformations (see, e.g., the techniques referenced in the General Synthetic Methods section). The alkyl diamine can also be replaced by other linkers that have terminal amines, including amine-terminated polyethylene glycol derivatives and the like. For example, the linker portion of the diamine-terminated linker can be an interrupted alkyl group such as a heteroalkyl diradical. The linker of the diamine-terminated linker can have the formula —NH—CH$_2$—X—NH— where X is a direct bond or a linker, wherein the linker is a divalent radical of the formula —W-A-W— wherein each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-3, or a direct bond; wherein each R' is independently H, (C$_1$-C$_6$)alkyl, or a nitrogen protecting group; and A is (C$_1$-C$_{20}$)alkyl, (C$_2$-C$_{16}$)alkenyl, (C$_2$-C$_{16}$)alkynyl, (C$_3$-C$_8$)cycloalkyl, (C$_1$-C$_{20}$)heteroalkyl, (C$_6$-C$_{10}$)aryl, —(OCH$_2$—CH$_2$)$_n$— where n is 1 to about 20, —C(O)NH(CH$_2$)$_n$ wherein n is 1 to about 6, —N(Me)(CH$_2$)$_n$— wherein n is 1 to about 6; or (C$_1$-C$_{20}$)alkyl, (C$_2$-C$_{16}$)alkenyl, (C$_2$-C$_{16}$)alkynyl, or —(OCH$_2$—CH$_2$)$_n$— interrupted between two carbons, or between a carbon and an oxygen, with a (C$_3$-C$_8$)cycloalkyl, heterocycle, or (C$_6$-C$_{10}$)aryl group. Techniques for conjugating the triazine diamine to the diamine linker are are standard transformations and are well known in the art. Such techniques are described by, for example, by Greg T. Hermanson in *Bioconjugate Techniques*, Academic Press, San Diego, Calif. (1996). Various linkers and methods for preparing covalent linkages are described in, for example, U.S. Pat. No. 7,282,339 (Beechem et al.); in *Peptides: Chemistry and Biology* by Sewald and Jakubke, Wiley-VCH, Weinheim (2002), pages 212-223; and in *Organic Synthesis on Solid Phase* by Dorwald, Wiley-VCH, Weinheim (2002).

In certain embodiments, the 6-chloro-1,3,5-triazine-2,4-diamine can be converted to aminoalkyl-1,3,5-triazine-2,4,6-triamines by exposing the 6-chloro-1,3,5-triazine-2,4-diamine to, for example, a diamine linker for a sufficient period of time at a sufficient temperature, which may depend on the specific alkyldiamine used. In some embodiments, the diamine linker can be an alkyldiamine of the structure NH$_2$—(CH$_2$)$_n$—NH$_2$ where n can be an integer from 1 to about 20. In further embodiments, the alkyldiamine can be methanediamine, ethane-1,2-diamine, propane-1,3-diamine, butane-1,4-diamine, pentane-1,5-diamine, hexane-1,6-diamine, heptane-1,7-diamine, octane-1,8-diamine, nonane-1,9-diamine, decane-1,10-diamine, undecane-1,11-diamine, dodecane-1,12-diamine, tridecane-1,13-diamine, tetradecane-1,14-diamine, and the like. The diamine need not be limited to a straight chain alkyl group tethering the amines. For example, the tether can be a branched alkyl group, a heteroalkyl group, a cycloalkyl group, an alkoxy group, an alkenyl group, an alkenyloxy group, an alkynyloxy group, an alkoxycarbonyl group, an alkylsulfinyl group, an alkylsulfonyl group, an alkynyl group, an alkylaminocarbonyl group, a cycloalkenyl group, a cycloalkylalkyl group, a heterocycloalkyl group, a heterocycloalkenyl group, for example, where the alkyl portion of the group comprises one to about twelve carbon atoms. Alternatively, the linker can be a divalent radical of the formula —W-A-W— as described above.

Salts and Solvates

Ligand A can be isolated as a pure compound or as a salt, for example, a hydrohalide salt, including salts with two, three, four or more equivalents of the hydrohalide, as appropriate.

Pharmaceutically acceptable salts of compounds described herein are within the scope of the invention and include acid or base addition salts which retain the desired pharmacological activity and are not biologically undesirable (e.g., the salt is not unduly toxic, allergenic, or irritating, and is bioavailable). When a compound has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the invention has an acidic group, such as for example, a carboxylic acid group, it can form salts with metals, such as alkali and earth alkali metals (e.g. Na$^+$, Li$^+$, K$^+$, ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds described herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Examples of suitable salts of the compounds described herein include their hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art. Also included are base addition salts such as sodium, potassium, calcium, ammonium, organic amino, or magnesium salt, or a similar salt.

When compounds described herein contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, behenic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention can contain both basic and acidic functionalities that allow the compounds to be converted into either base or acid addition salts.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms. In general, all physical forms are equivalent for the uses contemplated by the invention and are intended to be within the scope of the invention.

The term "solvate" refers to a solid compound that has one or more solvent molecules associated with its solid structure. Solvates can form when a compound is crystallized from a solvent. A solvate forms when one or more solvent molecules become an integral part of the solid crystalline matrix upon solidification. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. Hydrates can form when a compound is solidified or crystallized in water, where one or more water molecules become an integral part of the solid crystalline matrix. The compounds of the formulas described herein can be hydrates.

Pharmaceutical Formulations

The following describes information relevant to pharmaceutical and pharmacological embodiments and is further supplemented by information in the art available to one of ordinary skill. The exact formulation, route of administration and dosage can be chosen by an individual physician in view of a patient's condition (see e.g., Fingl et al., in *The Pharmacological Basis of Therapeutics*, 1975, Ch. 1).

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

A compound may be combined with different types of carriers depending on whether it is to be administered in solid, liquid or aerosol form, and whether it need to be sterile for such routes of administration as injection. Compounds and compositions described herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, *Remington's Pharmaceutical Sciences*, 18th Ed. Mack Printing Company, 1990).

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 1% to about 60%, or about 2% to about 25%, of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

It should be noted that the attending physician would know how to and when to terminate, interrupt, or adjust administration due to toxicity, or to organ dysfunctions, etc. Conversely, the attending physician would also know to adjust treatment to higher levels if the clinical response were not adequate (in light of or precluding toxicity aspects). The magnitude of an administered dose in the management of the disorder of interest can vary with the severity of the condition to be treated and to the route of administration. The severity of the condition may, for example, be evaluated, in part, by standard prognostic evaluation methods. Further, the dose and perhaps dose frequency, can also vary according to circumstances, e.g. the age, body weight, and response of the individual patient.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

Combination Therapy

Active ingredients described herein (e.g., compounds of Formula (I)) can also be used in combination with other active ingredients. Such combinations are selected based on the condition to be treated, cross-reactivities of ingredients and pharmaco-properties of the combination.

It is also possible to combine a compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and be "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic effect denotes an effect that is greater than the predicted purely additive effects of the individual compounds of the combination.

Combination therapy is further described by U.S. Pat. No. 6,833,373 (McKearn et al.), which includes additional active agents that can be combined with the compounds described herein, and additional types of ailments and other conditions that can be treated with a compound or combination of compounds described herein.

Accordingly, it is an aspect of this invention that an active agent (e.g., a compound of Formula I) can be used in combination with another agent or therapy method. An active agent may precede or follow the other agent treatment by intervals ranging from minutes to weeks. In embodiments where the other agent and expression construct are applied separately to a cell, one would generally ensure that a significant period of time did not elapse between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the disclosed active.

In some embodiments, one or more agents may be administered within about 1 minute, about 5 minutes, about 10 minutes, about 20 minutes about 30 minutes, about 45 minutes, about 60 minutes, about 2 hours, about 3 hours, about 4 hours, about 6 hours, about 8 hours, about 9 hours, about 12 hours, about 15 hours, about 18 hours, about 21 hours, about 24 hours, about 28 hours, about 31 hours, about 35 hours, about 38 hours, about 42 hours, about 45 hours, to about 48 hours or more prior to and/or after administering the disclosed active. In certain other embodiments, an agent may be administered within from about 1 day, about 2 days, about 3 days, about 4 days, about 5 days, about 6 days, about 8 days, about 9 days, about 12 days, about 15 days, about 16 days, about 18 days, about 20 days, to about 21 days prior to and/or after administering the disclosed active. In some situations, it may be desirable to extend the time period for treatment significantly, however, where several weeks (e.g., about 1, about 2, about 3, about 4, about 6, or about 8 weeks or more) lapse between the respective administrations.

Administration of the compositions of the invention to a patient will follow general protocols for the administration of chemotherapeutics, taking into account the toxicity, if any. It is expected that the treatment cycles would be repeated as necessary. It also is contemplated that various standard therapies or adjunct therapies, as well as surgical intervention, may be applied in combination with the described active agent. These therapies include but are not limited to chemotherapy, radiotherapy, immunotherapy, gene therapy and surgery.

Materials and Methods

The compounds described herein can be prepare as described above, using techniques known to those of skill in the art. Useful preparatory techniques and methods for assaying the compounds and their activity are described by Arambula et al., PNAS 2009, 106(38), 16068-16073 and Wong et al., *Nucleic Acids Res.* 2011, 39(20), 8881-8890. DNA oligomers can be obtained from Integrated DNA Technologies and can be purified by standard desalting. Purified RNA sequences can be obtained from Dharmacon Research Inc. (Lafayette, Colo.). Yeast tRNA can be obtained from Sigma-Aldrich.

Thermal Denaturation Studies. Thermal denaturation studies were performed with a temperature controlled Shimadzu 2501PC UV-Vis recording spectrophotometer enabled with an 8-well quartz sample cell (1.0 cm path, 130 µL total volume). Stock solutions of 800 µM DNA oligomers were prepared and annealed in a water bath >90° C. for 5 minutes then allowed to cool to ambient temperature. One equivalent of the respective ligand was added, followed by 20 µL of 100 mM MOPS pH 7.0, 10 µL of 3.0 M NaCl, and 10 µL of 10 mM EDTA. The samples were then diluted to 100 µL with water to give final concentrations of 12 µM DNA duplex, 12 µM ligand, 20 mM MOPS pH 7.0, 300 mM NaCl, and 1.0 mM EDTA. Samples were then placed in the 8-well cell and cooled to 0° C. The temperature dependent absorbance of each sample was monitored from 0° C. to 90° C. at 260 nm with a ramp rate of 1° C. per minute and monitoring every 0.5° C. The melting temperature of each curve (inflection point of the sigmoidal transition) can be determined by finding the maximum of the first derivative of the curve with Origin 7.0 (MicroCal, Inc. Northampton, Mass.).

Isothermal Titration Calorimetry. Isothermal titration calorimetry measurements were performed at 25° C. on a Micro-Cal VP-ITC (MicroCal, Inc., Northampton, Mass.). A standard experiment consisted of titrating 10 µL of a 500 µM ligand from a 250 µL syringe (rotating at 300 rpm) into a sample cell containing 1.42 mL of a 20 µM DNA/RNA solution. The duration of the injection was set to 24 s, and the delay between injections was 300 s. The initial delay prior to the first injection was 60 s. To derive the heat associated with each injection, the area under each isotherm (microcalories per second versus seconds) was determined by integration by the graphing program Origin 5.0 (MicroCal, Inc. Northampton, Mass.). The fitting requirements were such that the thermodynamic parameters were derived from curves that produced the lowest amount of deviation. In most cases, fitting to a sequential site binding model of two or three binding sites gave the most accurate data. In many cases, additional sites are not detected by Job plot analysis and likely represent low-affinity sites. Analogous low-affinity binding sites have previously been observed in aminoglycoside-16S rRNA interactions (Kaul et al. *Biochemistry* 2002, 41, 7695-7706). The ligand stock solution was 10 mM in DMSO. The buffer solution for ITC experiments was 20 mM MOPS pH 7.0, 300 mM NaCl and 5-10% DMSO to balance the residual DMSO in the ligand solution.

Fluorescence Experiments.

Fluorescence binding experiments and Job plot analysis were performed using a temperature controlled Horiba Jobin Yvon fluorimeter with a 250 µL cell with a 0.1 cm path.

Fluorescence binding experiments. A cell sample (250 µL) of 0.2 µM a compound of interest (in 20 mM MOPS pH 7.0, 300 mM NaCl) was excited at 310 nm (excitation slit of 4 nm)

and emission recorded between 470-530 nm (emission slit of 8 nm) monitoring the maximum at 495 nm. A concentrated sample of freshly annealed DNA/RNA was added as 1 μL injections via pipette. The sample was then allowed to equilibrate for 15 min and the fluorescence emission recorded. The decrease in fluorescence with increased DNA/RNA was monitored until the binding sites became saturated and the fluorescence change was no longer evident. Preparation of concentrated DNA/RNA samples: the DNA/RNA duplex (400 μM) was heated in a water bath (>90° C.) for 5 min then allowed to re-anneal by slowly cooling to ambient temperature. DNA/RNA samples ranging from 400-25 μM were prepared by serial dilution.

The % bound $(F-F_o/F_f-F_o)$ versus [DNA/RNA] was plotted and fit to the one binding site model:

$$y=(a^*x)/(K_d+x)$$

where a is the asymptotic limit. Experiments were performed in triplicate.

Job plot analysis. Stock solutions of both ligand and nucleic acid duplex were prepared in equal concentrations with 20 mM MOPS pH 7.0 and 300 mM NaCl. The DNA/RNA duplexes were annealed as previously described. Samples of varying molar ratios of ligand:DNA/RNA were prepared while the total concentration remains constant. The fluorescence of each sample was recorded in addition a control sample containing only the ligand. Plots of ΔF versus molar ratio were produced to determine binding stoichiometry of 1:1 or 2:1.

Protein Expression and Purification. An expression vector for MBNL1N (1-272 aminoacids) was obtained from Maurice S. Swanson (University of Florida, College of Medicine, Gainesville, Fla.). MBNL1N is comprised of the four zinc finger motifs of MBNL1 and contains a hexahis tag. The protein was expressed and purified as described previously (Yuan et al., *Nucleic Acids Res.* 2007, 35, 5474-5486). The molecular weight was confirmed by MALDI mass spectrometry and the concentration was determined by amino acid analysis.

Equilibrium Binding Assays. RNA was labeled with [γ-$^{32}$P]ATP using T4 polynucleotide kinase (New England Biolabs). Labeled RNA (5 μL, 0.5 nM) was heated at 95° C. for 2 min and then placed on ice for 10 min and diluted to 125 μL in RNA storage buffer (66 mM NaCl, 6.7 mM MgCl$_2$, and 27 mM Tris.HCl (pH 7.5). If required for the experiment, tRNA was added to the RNA solution to give a final concentration of approximately 8 μM. The protein (MBNL1N) was serially diluted in binding buffer (175 mM NaCl, 5 mM MgCl$_2$, 20 mM Tris.HCl (pH 7.5), 1.25 mM BME, 12.5% glycerol, 2 mg/mL BSA, and 0.1 mg/mL heparin), and 5 μL of protein solution was added to 5 μL of RNA solution (Warf and Berglund, RNA, 2007, 13, 2238-2251). The reaction mixture was incubated at room temperature for 25 min and loaded onto a 6% polyacrylamide gel (80:1) at 4° C. The gels were run for 1 hour at 360V in 22.5 mM Tris-borate buffer (pH 8). Gels were visualized on a Molecular Dynamics Storm phosphorimager. The apparent $K_d$ values were obtained by fitting fraction RNA bound versus protein concentration using the following equation: fraction bound=$1/(1+(K_d/[P]_T))$. All binding measurements were performed with a greater than 10-fold excess of protein over RNA in each binding reaction used to determine the $K_d$ so that [P] would be approximately equal to $[P]_{total}$.

Inhibition Assays. The inhibition of the MBNL1N-RNA complex was investigated using the above procedure except that the small molecule was added to the RNA-protein complex after 25 min of incubation. The reaction mixture was incubated for an additional 10-15 minutes at room temperature (~23° C.). The inhibition assays were performed in the presence of 10% DMSO. To determine IC$_{50}$ values, the free RNA versus small molecule concentration was fit to the equation: B=ΔB exp((-0.69/IC$_{50}$)C)+B$_f$. B is the volume of the free RNA band in the gel, ΔB is the difference between the volumes of the free RNA bands at the lowest and highest concentrations of small molecule (B$_i$—B$_f$), C is the concentration of the small molecule, and IC$_{50}$ is the concentration of small molecule at which B=(½ΔB)+B$_f$. The apparent inhibition constant (K$_i$) was determined using the equation: K$_i$=IC$_{50}$/(1+([P]$_T$/K$_d$), where [P]$_T$ is the total concentration of protein and K$_d$ is the dissociation constant of the MBNL1N-RNA complex.

U1A and Sex lethal proteins were expressed as hexa-his constructs and were purified using a Ni-NTA column from Qiagen. For U1A, inhibition assays were performed as reported previously for gel shift binding assays with 20 nM U1A (Shiels et al., *Nucleic Acids Res,* 2002, 30, 550-558). The K$_d$ of the U1A-SL2 RNA complex under these conditions is 0.5 nM. For Sex lethal, inhibition assays were performed in 15 mM HEPES, pH 7.6, 50 mM potassium chloride, 1 mM EDTA, 1 mM β-mercaptoethanol, 20% glycerol, and 0.005% Triton-X, with 0.2 μg/μL t-RNA with 250 nM Sex lethal protein and 0.2 nM $^{32}$P-labeled tra RNA. Under these conditions, the K$_d$ of the Sex lethal-tra RNA complex is 70 nM.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Preparation of Ligand 1

Ligand 1 can be prepared as illustrated in the following schemes.

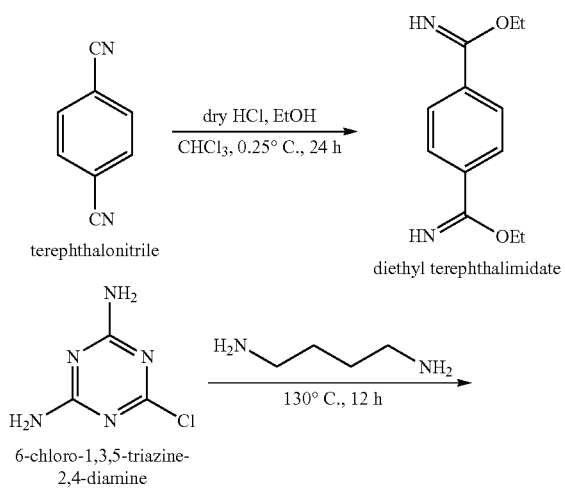

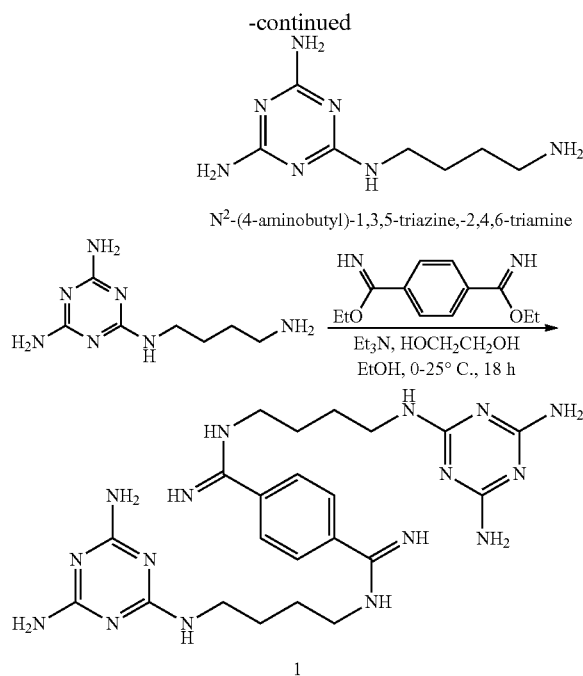

N²-(4-aminobutyl)-1,3,5-triazine,-2,4,6-triamine

The product can be isolated as a free base (ligand 1) (N¹, N⁴-bis(4-((4,6-diamino-1,3,5-triazin-2-yl)amino)butyl) terephthalimidamide) or as a bis-HCl salt (2).

Example 2

Preparation of Ligands A

Ligands A can be prepared as illustrated in the following schemes. For example, compounds of Formula I can be prepared by exposing 6-chloro-1,3,4-triazine-2,4-diamine to a linker compound having a structure according to $NH_2$-L-$NH_2$, wherein L is a linker as described for Formula I. The resulting compound, for example, the triazine having an amine-terminating linker as shown in the scheme below, can then be conjugated to a bis-alkyl or bis-aryl terephthalimidate.

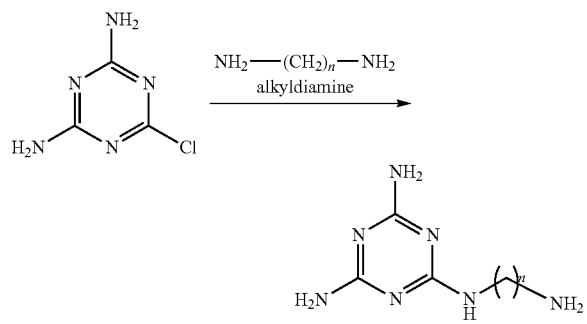

where n is 1 to about 12.

Other dialkylamine linkers can be used as described above. The product can then be conjugated with an optionally substituted dialkyl or diaryl terephthalimidate, as illustrated below, where R is alkyl or aryl, R¹ is a substituent as described herein, and m is 0, 1, 2, 3 or 4.

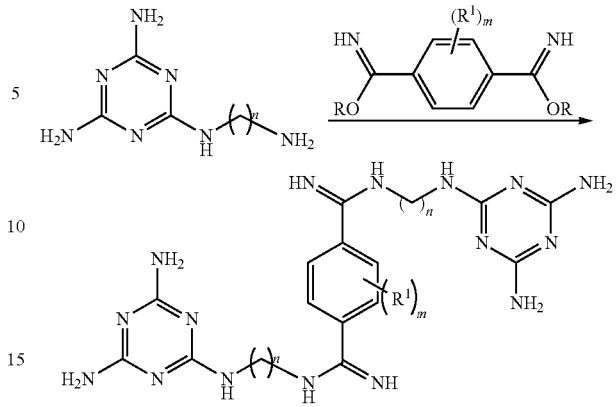

where n is 1 to about 12.

The product can be isolated as a free base or as a bis- or tetra-salt, as appropriate.

Example 3

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula (I):

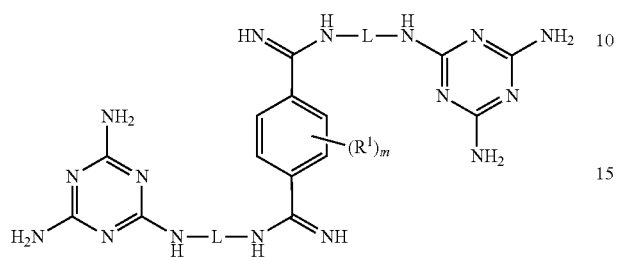

wherein
m is 0, 1, 2, 3, or 4;
each $R^1$ is independently alkyl, cycloalkyl, aryl, heteroaryl, heterocycle, halo, hydroxyl, nitro, cyano, alkoxy, carboxy, trifluoromethyl, trifluoromethoxy, amino, or aminoalkyl; and
each L is independently a divalent alkyl or a divalent radical of the formula —W-A-W— wherein each W is independently —N(R")C(=O)—, —C(=O)N(R")—, —OC(=O)—, —C(=O)O—, —S(O)—, —S(O)$_2$—, —N(R")—, —C(=O)—, —(CH$_2$)$_n$— where n is 1-10, or a direct bond; wherein each R" is independently H, (C$_1$-C$_6$)alkyl, or a nitrogen protecting group; and A is (C$_1$-C$_{20}$)alkyl, (C$_2$-C$_{16}$)alkenyl, (C$_2$-C$_{16}$)alkynyl, (C$_3$-C$_8$)cycloalkyl, (C$_1$-C$_{20}$)heteroalkyl, (C$_6$-C$_{10}$)aryl, —(OCH$_2$—CH$_2$)$_n$— where n is 1 to about 20, —C(O)NH(CH$_2$)$_n$ wherein n is 1 to about 6, —N(Me)(CH$_2$)$_n$ wherein n is 1 to about 6; or (C$_1$-C$_{20}$)alkyl, (C$_2$-C$_{16}$) alkenyl, (C$_2$-C$_{16}$)alkynyl, or —(OCH$_2$—CH$_2$)$_n$—interrupted between two carbons, or between a carbon and an oxygen, with a heterocycle, or (C$_6$-C$_{10}$)aryl group;
or a pharmaceutically acceptable salt thereof.

2. The compound of claim 1 wherein L is (C$_1$-C$_{12}$)alkyl.

3. The compound of claim 1 wherein L is (C$_3$-C$_{10}$)alkyl.

4. The compound of claim 1 wherein L is —CH$_2$—(OCH$_2$—CH$_2$)$_n$—OCH$_2$— where n is 1 to 20.

5. The compound of claim 1 wherein m is 0.

6. The compound of claim 1 wherein m is 1, 2, 3, or 4.

7. The compound of claim 1 wherein $R^1$ is methyl, ethyl, cyclopropyl, phenyl, benzyl, pyridyl, furanyl, F, Cl, Br, OH, NO$_2$, CN, methoxy, ethoxy, carboxy, trifluoromethyl, trifluoromethoxy, amino, or methylamino.

8. A compound of Formula (II):

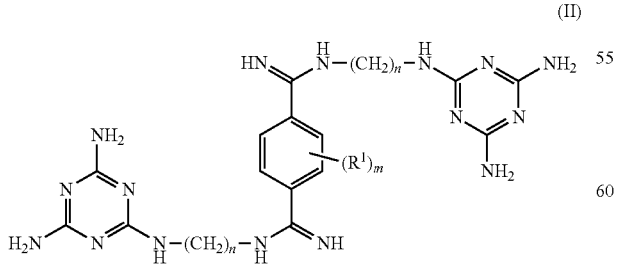

wherein
m is 0, 1, 2, 3, or 4;
each $R^1$ is independently alkyl, cycloalkyl, aryl, heteroaryl, heterocycle, halo, hydroxyl, nitro, cyano, alkoxy, carboxy, trifluoromethyl, trifluoromethyl, amino, or aminoalkyl; and
each n is independently 3, 4, 5, 6, 7, 8, 9, or 10;
or a pharmaceutically acceptable salt thereof.

9. The compound of claim 8 wherein the compound of Formula (II) is a compound of Formula (III):

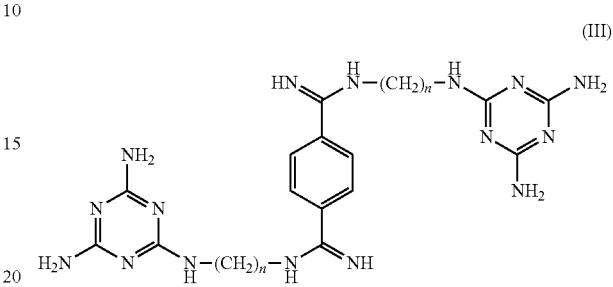

wherein
each n is independently 3, 4, or 5;
or a pharmaceutically acceptable salt thereof.

10. The compound of claim 9 wherein each n is 3.
11. The compound of claim 9 wherein each n is 4.
12. The compound of claim 9 wherein each n is 5.
13. A composition comprising a compound of claim 8 and a pharmaceutically acceptable diluent or carrier.
14. A composition comprising a compound of claim 11 and a pharmaceutically acceptable diluent or carrier.
15. A method to inhibit muscleblind-like (MBNL) protein binding comprising contacting MBNL protein with an effective inhibitory amount of a compound of claim 8, thereby inhibiting the binding activity of the muscleblind-like (MBNL) protein.
16. A method to selectively form a complex with CUG repeats in RNA, or CTG repeats in DNA, comprising contacting the RNA or DNA with a compound of claim 8, thereby forming a complex of the compound and the RNA, or a complex of the compound and the DNA, wherein the complexation inhibits RNA replication or DNA replication.
17. The method of claim 16 wherein the affinity of the compound for the CUG repeat in RNA is less than about 1 micromolar.
18. The compound of claim 8 wherein the compound is compound 1:

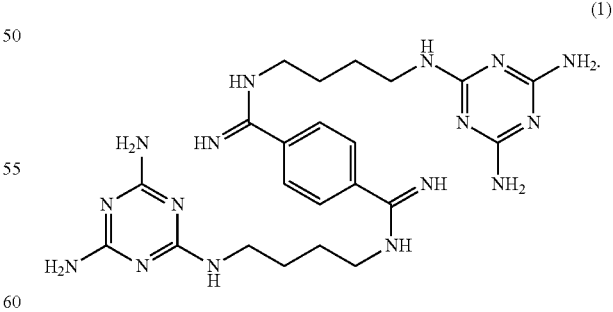

19. A composition comprising a compound of claim 18 and a pharmaceutically acceptable diluent or carrier.
20. A composition comprising a compound of claim 1 and a pharmaceutically acceptable diluent or carrier.